United States Patent [19]

Bagli et al.

[11] 4,057,556

[45] Nov. 8, 1977

[54] TROPONYL-OXAMIC ACID DERIVATIVES

[75] Inventors: Jehan F. Bagli, Kirkland; Tibor Bogri, Montreal, both of Canada

[73] Assignee: Ayerst, McKenna & Harrison Ltd., Montreal, Canada

[21] Appl. No.: 697,296

[22] Filed: June 17, 1976

[51] Int. Cl.$^2$ .............................................. C07C 103/42
[52] U.S. Cl. ................ 424/305; 260/514 J; 260/516; 260/518 R; 260/514; 260/556 AR; 260/563 R; 260/570.5 CA; 260/568; 260/590 C; 424/309; 424/319; 560/9; 560/12; 560/39; 560/41; 560/125
[58] Field of Search ............ 260/468 E, 468 J, 514 J, 260/470, 471 A, 518 R, 517, 516; 424/305, 319, 309

[56] References Cited

U.S. PATENT DOCUMENTS

| 3,966,965 | 6/1976 | Sellstedt et al. | 424/309 |
| 3,993,679 | 11/1976 | Hall et al. | 260/405 |

*Primary Examiner*—Robert Gerstl
*Attorney, Agent, or Firm*—Stephen Venetianer

[57] ABSTRACT

Tropone derivatives characterized by having a derivative of oxamic acid at positions 2 and/or 5 are disclosed. In addition, the tropone nucleus can be optionally further substituted. The foregoing compounds are useful for preventing or treating allergic conditions in a mammal. Methods for the preparation and use of said compounds are disclosed.

26 Claims, No Drawings

TROPONYL-OXAMIC ACID DERIVATIVES

BACKGROUND OF THE INVENTION a. Field of the Invention

This invention relates to novel tropone derivatives, to processes for their preparation, to methods for using said derivatives, and to therapeutically acceptable salts and compositions of said derivatives.

More specifically, the present invention relates to novel troponyl-oxamic acid derivatives possessing valuable pharmacologic properties. For example, these derivatives are useful for preventing or treating allergic conditions in a mammal at dosages which do not elicit undesirable side effects. The combination of these pharmacologic properties render the troponyl-oxamic acid derivatives of the invention therapeutically useful.

b. Description of the Prior Art

A rather large number of reports dealing with tropone derivatives are available. The prior art relating to tropone derivatives is summarized in various reviews; for example, see the review by F. Pietra in Chem. Rev., 73, 293 (1973). Another report describes a class of alkyl esters of 5-aminotropolones which exhibit anti-neoplastic activity, see L. D. Donaruma, Canadian Patent No. 787,451, issued June 11, 1968.

The tropone derivatives of the present invention are distinguished from the prior art compounds by the nature of the substituents on the tropone nucleus and by their pharmacologic properties. More specifically, the novel tropone derivatives of this invention are distinguished from the prior art compounds by having the tropone nucleus substituted with one or two oxamic acid derivatives.

SUMMARY OF THE INVENTION

The compounds of this invention are represented by formula I

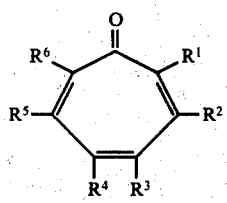
(I)

in which $R^1$ and $R^4$ are the same or different selected from the group consisting of hydrogen, halo, trifluoromethyl, lower alkoxy, lower alkyl, phenyl, hydroxy, phenoxy, mercapto, (2-carboxyphenyl)thio, $NR^7R^8$ wherein $R^7$ and $R^8$ each is hydrogen or lower alkyl, or $R^7$ is lower alkyl and $R^8$ is p-toluenesulfonyl, and a radical of formula $NR^9COCOOR^{10}$ wherein $R^9$ and $R^{10}$ each is hydrogen or lower alkyl; and $R^2$, $R^3$, $R^5$ and $R^6$ are the same or different selected from the group consisting of hydrogen, halo, trifluoromethyl, lower alkoxy, lower alkyl, phenyl, hydroxy, phenoxy, mercapto, (2-carboxyphenyl)thio, and $NR^7R^8$ wherein $R^7$ and $R^8$ each is hydrogen or lower alkyl; or $R^7$ is lower alkyl and $R^8$ is p-toluenesulfonyl; with the proviso that at least one of $R^1$ and $R^4$ must be a radical of formula $NR^9COCOOR^{10}$ wherein $R^9$ and $R^{10}$ are as defined herein.

A preferred group of compounds of formula I are those in which at least three of $R^1$, $R^2$, $R^3$, $R^4$, $R^5$ and $R^6$ are hydrogen.

Another preferred group of compounds of this invention is represented by formula I in which a. $R^1$ is a radical of formula $NR^9COCOOR^{10}$ in which $R^9$ and $R^{10}$ are the same or different and are hydrogen or lower alkyl, and $R^2$, $R^3$, $R^4$, $R^5$ and $R^6$ are the same or different selected from the group consisting of hydrogen, lowr alkoxy and hydroxy; or b. $R^4$ is a radical of formula $NR^9COCOOR^{10}$ in which $R^9$ and $R^{10}$ each is hydrogen or lower alkyl and $R^1$, $R^2$, $R^3$, $R^5$ and $R^6$ are the same or different selected from the group consisting of hydrogen, lower alkoxy and hydroxy; or c. $R^1$ and $R^4$ are a radical of formula $NR^9COCOOR^{10}$ wherein $R^9$ and $R^{10}$ each is hydrogen or lower alkyl, and $R^2$, $R^3$, $R^5$ and $R^6$ are the same or different selected from the group consisting of hydrogen, lower alkoxy and hydroxy.

Still another preferred group of compounds of this invention are represented by formula I in which a. $R^1$ is a radical of formula $NR^9COCOOR^{10}$ in which $R^9$ and $R^{10}$ each is hydrogen or lower alkyl, and $R^2$, $R^3$, $R^4$, $R^5$ and $R^6$ are the same or different selected from the group consisting of hydrogen, lower alkoxy and hydroxy, with the proviso that at least three of $R^2$, $R^3$, $R^4$, $R^5$ and $R^6$ are hydrogen; or b. $R^4$ is a radical of formula $NR^9COCOOR^{10}$ in which $R^9$ and $R^{10}$ each is hydrogen or lower alkyl, and $R^1$, $R^2$, $R^3$, $R^5$ and $R^6$ are the same or different selected from the group consisting of hydrogen, lower alkoxy and hydroxy, with the proviso that at least three of $R^1$, $R^2$, $R^3$, $R^5$ and $R^6$ are hydrogen; or c. $R^1$ and $R^4$ are a radical of formula $NR^9COCOOR^{10}$ wherein $R^9$ and $R^{10}$ each is hydrogen or lower alkyl; and $R^2$, $R^3$, $R^5$ and $R^6$ are the same or different selected from the group consisting of hydrogen, lower alkoxy and hydroxy, with the proviso that at least two of $R^2$, $R^3$, $R^5$ and $R^6$ are hydrogen.

The therapeutically acceptable salts of the compounds of formula I are also included within the scope of this invention.

The compounds of this invention of formula I are prepared by a process comprising: condensing a compound of formula II

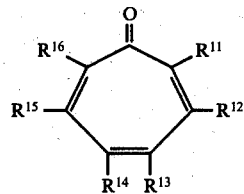
(II)

in which $R^{11}$ and $R^{14}$ are the same or different selected from the group consisting of hydrogen, halo, trifluoromethyl, lower alkoxy, lower alkyl, phenyl, hydroxy phenoxy, mercapto, (2-carboxyphenyl)thio, $NR^7R^8$ wherein $R^7$ is lower alkyl and $R^8$ is hydrogen, lower alkyl or p-toluenesulfonyl, and $NHR^9$ wherein $R^9$ is hydrogen or lower alkyl; and $R^{12}$, $R^{13}$, $R^{15}$ and $R^{16}$ are the same or different selected from the group consisting of hydrogen, halo, trifluoromethyl, lower alkoxy, lower alkyl, phenyl, hydroxy, phenoxy, mercapto, (2-carboxyphenyl)thio, and $NR^7R^8$ wherein $R^7$ is lower alkyl and $R^8$ is hydrogen, lower alkyl or p-toluenesulfonyl; with the priviso that at least one of $R^{11}$ and $R^{14}$ must be $NHR^9$, with a compound of formula III Halogen—COCOOR$^{10}$ (III)

in which R$^{10}$ is lower alkyl and the halogen is bromine, chlorine or iodine in the presence of a proton acceptor to obtain the corresponding compound of formula I in which R$^1$ and R$^4$ are the same or different selected from the group consisting of hydrogen, halo, trifluoromethyl, lower alkoxy, lower alkyl, phenyl, hydroxy, phenoxy, mercapto, (2-carboxyphenyl)thio and NR$^7$R$^8$ wherein R$^7$ is lower alkyl and R$^8$ is hydrogen, lower alkyl or p-toluenesulfonyl, and a radical of formula NR$^9$COCOOR$^{10}$ wherein R$^9$ is as defined herein and R$^{10}$ is lower alkyl; and R$^2$, R$^3$, R$^5$ and R$^6$ are the same or different selected from the group consisting of hydrogen, halo, trifluoromethyl, lower alkoxy, lower alkyl, phenyl, hydroxy, phenoxy, mercapto, (2-carboxyphenyl)thio and NR$^7$R$^8$ wherein R$^7$ is lower alkyl and R$^8$ is hydrogen, lower alkyl or p-toluenesulfonyl; and, if desired and required, followed by transformation of the compound of formula I, prepared as described above, to other compounds of formula I by methods described herein.

Another aspect of this invention involves a pharmaceutical composition comprising a compound of formula I or a therapeutically acceptable addition salt thereof, and a pharmaceutically acceptable carrier therefor.

Still another aspect of this invention involves a method for preventing or treating allergic conditions in a mammal which comprises administering to said mammal an effective allergy alleviating amount of a compound of formula I or a therapeutically acceptable addition salt thereof.

DETAILED DESCRIPTION OF THE INVENTION

The term "lower alkyl" as used herein contemplates both straight and branched chain alkyl radicals containing from one to six carbon atoms and includes methyl, ethyl, propyl, isopropyl, butyl, isobutyl, pentyl, hexyl and the like.

The term "lower alkoxy" as used herein contemplates both straight and branched chain alkoxy radicals containing from one to six carbon atoms and includes methoxy, ethoxy, isopropoxy, butoxy, hexanoxy and the like.

The terms "halogen" and "halo" as used herein contemplate halogens and include fluorine, chlorine, bromine and iodine, unless stated otherwise.

The term "lower alkanol" as used herein contemplates both straight and branched chain alkanols containing from one to six carbon atoms and includes methanol, ethanol, isopropanol, butanol, hexanol and the like.

The acidic compounds of formula I in which R$^1$ and/or R$^4$ is a radical of formula NR$^9$COCOOR$^{10}$ wherein R$^{10}$ is hydrogen form salts with suitable therapeutically acceptable inorganic and organic bases. These derived salts possess the same activity as the parent acid and are included within the scope of this invention. The acid is transformed in excellent yield into the corresponding therapeutically acceptable salt by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the alkali metals or alkaline earth metals, for example, sodium, potassium, magnesium, calcium and the like. Suitable organic bases include the following amines; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di and trialkanolamines, the alkanol radicals of which contain up to three carbon atoms, for example, mono-, di- and triethanolamine; alkylene-diamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methyl-morpholine and N-(2-hydroxyethyl)piperidine, as well as pyridine. Furthermore, there may be mentioned the corresponding quaternary salts, such as the tetraalkyl (for example tetramethyl), alkyl-alkanol (for example methyltrimethanol and trimethyl-monoethanol) and cyclic ammonium salts, for example the N-methylpyridinium, N-methyl-N-(2-hydroxyethyl)morpholinium, N,N-dimethylmorpholinium, N-methyl-N-(2-hydroxyethyl)morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid for formula I in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acid of formula I is dissolved in a suitable solvent of either moderate or lower polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of lower polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula I with an equivalent amount of the corresponding quaternary ammonium hydroxide in water solution, followed by evaporation of the water.

The basic compounds of formula I in which R$^1$, R$^2$, R$^3$, R$^4$, R$^5$ and/or R$^6$ is NR$^7$R$^8$ wherein R$^7$ and R$^8$ are as defined herein form addition salts with suitable inorganic and organic acids. These salts possess the same activities as the parent base compound when administered to a mammal and may be utilized in the same manner. Suitable acids to form these salts include, for example the common mineral acids, hydrophalic, sulfuric or phosphoric, as well as the organic acids, formic, acetic, maleic, malic, citric, or tartaric acid, or acids which are sparingly soluble in body fluids and which impart slow-release properties to their respective salts such as pamoic or tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

Also included within the scope of this invention are the isomers of the compounds of formula I resulting from the asymmetric centers contained therein.

Also included within the scope of this invention are the tautomeric forms of the compounds of formula I in which $R^1$, $R^2$, $R^3$, $R^4$, $R^5$ and/or $R^6$ is hydroxy resulting from the keto-enol equilibrium contained therein.

Anti-allergic Activity

The compounds of this invention of formula I or therapeutically acceptable salts thereof are useful in the prevention or treatment of allergic reactions in a mammal upon oral or parenteral administration.

More specifically, the compounds of this invention are useful for the prophylactic treatment as well as for the management of anaphylactic reactions and atopic allergic manifestations, for example, bronchial asthma, hay fever, allergic rhinitis, allergic conjunctivitis, food allergies, urticaria and the like, in a sensitized mammal.

More specifically exemplified, the compounds of this invention are effective anti-allergic agents when tested using the passive cutaneous anaphylaxis (PCA) method, described by I. Mota, Immunology, 7, 681(1964). The anti-allergic activity of a given compound is measured in rats by its ability to inhibit the increase in vascular permeability at the site of injection of rat immunoglobulin E (IgE) followed by i.v. administration of the specific antigen. Evans blue is injected i.v. at the same time as the specific antigen, and the size of the wheal or of the area infiltrated with Evans blue is measured and compared with that of untreated controls. An effective anti-allergic agent will prevent or inhibit the release of inflammatory mediators (mainly serotonin and histamine from the mast cells) which causes an increase in vascular permeability and thus an infiltration of Evans blue surrounding the site of injection of IgE. The anti-allergic activity of the compounds of formula I is demonstrated by the reduction of the wheal size of sensitized skin tissue compared to that of control animals. A comparison of the anti-allergic activity of the compounds of this invention with the anti-allergic activity of a standard compound, such as disodium cromoglycate, indicates that the compounds of this invention function in the same manner as disodium cromoglycate by blocking the release of mediators from the mast cells responsible for the allergic reaction.

When the compounds of formula I of this invention are used for suppressing allergic manifestations of anaphylactic reactions and atopic hypersensitivity in a mammal, they are used alone or in combination with pharmacologically acceptable carriers, the proportion of which is determined by the solubility and the chemical nature of the compound, chosen route of administration and standard biological practice. For example, they are administered parenterally by injection; orally; by the nasal route, for instance, as drops or aerosol; or by inhalation from an aerosol.

In addition, the compounds of this invention can be administered in conjunction with common anti-allergics, for example, known compounds effecting anti-histaminic, analgesic, central nervous system depressant, anti-hypertensive, immunosupressive, anti-bradykinin, anti-serotonin or endocrinological responses.

Therapeutic compositions containing the compounds of this invention are effective anti-allergic agents for preventing or relieving anaphylactic allergic manifestations at dosages of 0.1 mg to 100 mg/kg body weight when administered parenterally to a mammal. For administration to a mammal by parenteral injection, it is preferred to use the compounds of formula I in solution in a sterile aqueous vehicle which may also contain other solutes such as buffers or preservatives, as well as sufficient quantities of pharmaceutically acceptable salts or of glucose to make the solution isotonic.

A number of the compounds of this invention of formula I are useful in the management of allergic reactions when administered orally at dosages of 0.5 mg to 500 mg/kg body weight to a sensitized mammal. For example, the representative compounds of formula I,

[(2-oxo-3,5,7-cycloheptatrien-1-yl)amino]oxo-acetic acid ethyl ester (see Example 1),
[N-(2-oxo-3,5,7-cycloheptatrien-1-yl)-N-methylamino]-oxo-acetic acid ethyl ester (see Example 1),
2,2'-[(2-oxo-3,5,7-cycloheptatrien-1,5-diyl)diimino]-bis[2-oxo-acetic acid] diethyl ester (see Example 6),
[(2-oxo-3,5,7-cycloheptatrien-1-yl)amino]oxo-acetic acid pentyl ester (see Example 31) and
[(5-methoxy-4-oxo-2,5,7-cycloheptatrien-1-yl)amino]-oxo-acetic acid 1-methylethyl ester (see Example 31), are effective anti-allergic agents when administered orally at dosages of 1.0 mg to 100 mg/kg body weight.

When the compounds of this invention are employed as anti-allergic agents in mammals, e.g. rats, orally effective, anti-allergic amounts of the compounds are administered to the mammal, either alone or combined with pharmaceutically acceptable excipients in a dosage form, i.e. capsule or tablet, or the compounds are administered orally in the form of solutions or suspensions.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets may be uncoated or they may be coated by known techniques so as to delay disintegration and absorption in the gastrointestinal tract and thereby provide a sustained action over a longer period.

The aqueous suspensions of the invention contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions may also contain one or more preservatives, one of more coloring agents, one or more flavoring agents and one or more sweetening agents.

Non-aqueous suspensions may be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions may also contain a sweetening agent, a flavoring agent and an anti-oxidant.

The compounds of formula I can also be administered as nasal powders or insufflations. For such purpose the compounds are administered in finely divided solid form together with a pharmaceutically acceptable solid carrier, for example, a finely divided polyethylene glycol ("Carbowax 1540") or finely divided lactose. Such compositions may also contain other excipients in finely divided solid form, for instance, preservatives, buffers, or surface active agents.

When administering the compounds of this invention by inhalation from an aerosol, the compound of formula I is dissolved in water or ethanol and mixed with a volatile propellant, for example, dichlorotetrafluoroethane and dichlorodifluoromethane, and placed in a pressurized container having a metering valve to release a predetermined amount of material.

The dosage of the compounds of this invention will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstance is reached. In general, the compounds of this invention are most desirably administered at a concentration level that will generally afford effective results without causing any harmful or deleterious side effects, and preferably at a level that is in a range of from about 0.1 mg to about 500 mg per kilogram body weight, although as aforementioned variations will occur. However, a dosage level that is in the range of from about 0.5 mg to about 200 mg per kilogram body weight is most desirably employed in order to achieve effective results.

Processes

Useful and practical starting materials for the preparation of the compounds of this invention of formula I are the tropone derivatives of formula II

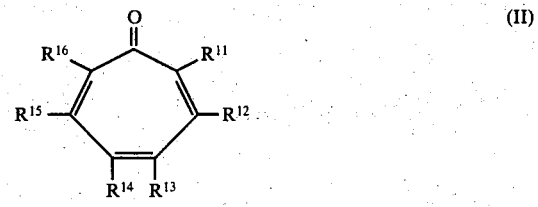

(II)

in which $R^{11}$, $R^{12}$, $R^{13}$, $R^{14}$, $R^{15}$ and $R^{16}$ are as defined in the first instance.

The tropone derivatives of formula II suitable as starting materials are described in a number of reports; for example, see the recent review on tropone derivatives, their preparation and their interconversions by F. Pietra, supra. Thus, the tropone derivatives suitable as starting materials are either known or they can be prepared by conventional means.

The compounds of this invention of formula I are prepared by condensing the compound of formula II in which $R^{11}$, $R^{12}$, $R^{13}$, $R^{14}$, $R^{15}$ and $R^{16}$ are as defined in the first instance with one to ten molar equivalents, preferably one to three molar equivalents, of a compound of formula III.

Halogen—COCOOR$^{10}$   (III)

in which $R^{10}$ is lower alkyl and the halogen is bromine, chlorine or iodine in the presence of a proton acceptor to obtain the corresponding compound of formula I in which $R^1$ and $R^4$ are the same or different selected from the group consisting of hydrogen, halo, trifluoromethyl, lower alkoxy, lower alkyl, phenyl, hydroxy, phenoxy, mercapto, (2-carboxyphenyl)thio and $NR^7R^8$ wherein $R^7$ is lower alkyl and $R^8$ is hydrogen, lower alkyl or p-toluenesulfonyl, and a radical of formula $NR^9COCOOR^{10}$ wherein $R^9$ is as defined herein and $R^{10}$ is lower alkyl; and $R^2$, $R^3$, $R^5$ and $R^6$ are the same or different selected from the group consisting of hydrogen, halo, trifluoromethyl, lower alkoxy, lower alkyl, phenyl, hydroxy, phenoxy, mercapto, (2-carboxyphenyl)thio and $NR^7R^8$ wherein $R^7$ is lower alkyl and $R^8$ is hydrogen, lower alkyl or p-toluenesulfonyl.

In practicing the above condensation it is preferable to use an inert solvent as a reaction medium. Suitable solvents include benzene, toluene, chloroform, methylene chloride, lower alkyl ketones (i.e. 2-propanone, 2-butanone and 3-pentanone) and the like. However, if the reactants are mutually soluble, the solvent can be omitted without deleterious effects.

Suitable proton acceptors include the organic bases, or amines for instance, triethylamine, pyridine, N-ethylmorpholine, 1,5-diazabicyclo[3.4.0]nonene-5 and the like, as well as the inorganic bases, preferably the alkali metal hydroxides, carbonates, hydrides, amides and alkoxides, for example, sodium ethoxide, sodium hydroxide, potassium hydroxide, potassium carbonate, sodium methoxide and the like. The preferred proton acceptors employed are the organic bases or amines. The amount of the organic bases can vary from one molar equivalent to a large molar excess. When a large molar excess is used, the organic base can also serve as the solvent for the condensation.

The duration and temperature of the condensation are not critical; however, the preferred time is from about ten minutes to about 2 days and the temperature can range from about −10° C to 100° C or the boiling point of the reaction mixture, preferably from about 20° C to the boiling point of the reaction mixture. The compounds of formula I are separated from the reaction mixture by conventional means, for example, evaporation, filtration, extraction, chromatography and/or crystallization.

The compounds of formula I obtained from the above described condensation can be further reacted to obtain other compounds of formula I by methods described hereinafter.

For instance the compound of formula I in which at least one of $R^1$, $R^2$, $R^3$, $R^4$, $R^5$ and $R^6$ is lower alkoxy or halo can be reacted with a molar excess of ammonia or an amine of formula $HNR^7R^8$ in which $R^7$ and $R^8$ are as defined herein to obtain the corresponding compound of formula I in which at least one of $R^1$, $R^2$, $R^3$, $R^4$, $R^5$ and $R^6$ is $NR^7R^8$ in which $R^7$ and $R^8$ are as defined herein. The reaction is conducted either using the amine of formula $HNR^7R^8$ as solvent or a suitable solvent can be selected from water and a lower alkanol (i.e. methanol, ethanol and the like). Suitable conditions for the reaction are a temperature of from about −50° C to about 100° C, preferably 0° to 100° C, for about ten minutes to 12 hours. If the temperature necessary for reaction is above the boiling point of the reaction mixture, the reaction can be conducted at the desired temperature in a pressure vessel without deleterious effects.

The compound of formula I, prepared as above, in which at least one of $R^1$ and $R^4$ is a radical of formula $NR^9COCOOR^{10}$ wherein $R^9$ is as defined herein and $R^{10}$ is lower alkyl can be hydrolyzed to obtain the corresponding acidic compound of formula I in which the corresponding $R^1$ and $R^4$ is a radical of formula $NR^9COCOOR^{10}$ wherein $R^9$ is as defined herein and $R^{10}$ is hydrogen. The preferred method of hydrolysis comprises the use of 0.1 to 2.0 molar equivalents, preferably 0.5 to 1.0 molar equivalents, of a mild alkali, for example a suitable mild alkali selected from the bicarbonates and acetates of sodium or potassium, in an inert solvent, for instance, water, a lower alkanol (i.e. methanol or ethanol) or mixtures thereof, at a temperature of about 20° to 120° C for about 1 to 10 hours. Acidification of the reaction mixture with a dilute mineral acid, such as hydrochloric acid, sulfuric acid, phosphoric acid and the like, gives the corresponding acidic compound of formula I.

In addition, a number of the compounds of formula I are readily converted to other compounds of formula I. In some cases it is convenient and preferable to prepare a specific compound of formula I by the transformation of another compound of formula I. Examples of such interconversions of the compound of formula I are described hereinafter.

For example, the acidic compound of formula I described above (i.e. $R^1$ and/or $R^4$ is a radical of formula $NR^9COCOOR^{10}$ wherein $R^9$ is as defined herein and $R^{10}$ is hydrogen) is readily esterified to obtain the corresponding ester of formula I (i.e. $R^1$ and/or $R^4$ is a radical of formula $NR^9COCOOR^{10}$ wherein $R^9$ is as defined herein and $R^{10}$ is lower alkyl). Suitable esterification conditions include a variety of methods; for example, ester exchange, treatment with diazomethane, or conversion of the acid to the corresponding activated carbonyl (i.e., acid halide, anhydride, succinimio, imidazolide and the like), followed by treatment of the latter with an appropriate lower alkanol, see also L. F. Fieser and M. Fieser, "Advanced Organic Chemistry," Reinhold Publishing Corporation, New York 1961, pp. 370–381.

A preferred and convenient method of esterification comprises dissolving the acidic compound of formula I in an inert solvent, preferably dimethylsulfoxide, in the presence of one to ten molar equivalents of a mild base, for example, sodium or potassium carbonate. One to three molar equivalents of a lower alkyl bromide or chloride is added and the solution is maintained at a temperature of about 20° to 100° C, preferably at about 40° to 80° C, for about 30 minutes to 5 hours.

The compound of formula I in which at least one of $R^1$, $R^2$, $R^3$, $R^4$, $R^5$ and $R^6$ is hydroxy can be alkylated to obtain the corresponding compound of formula I in which the corresponding $R^1$, $R^2$, $R^3$, $R^4$, $R^5$ and $R^6$ is alkoxy. The alkylation is conveniently carried out by reacting said hydroxy compound with one to five molar equivalents of a di(lower)alkyl sulfate in the presence of one to five molar equivalents of a mild alkali, for instance sodium or potassium carbonate in an inert solvent, for example, a lower alkyl ketone, preferably 2-butanone, 2-propanone and the like. The alkylation is conducted at a temperature from about 30° C to the boiling point of the reaction mixture for about 30 minutes to ten hours.

A useful alternative method of esterification or alkylation comprises reacting the acidic or hydroxy compound of formula I with an excess of a diazoalkane, for instance diazomethane, diazoethane and the like, in an inert solvent, e.g. diethyl ether or methanol.

The compound of formula I in which at least one of $R^1$, $R^2$, $R^3$, $R^4$, $R^5$ and $R^6$ is lower alkoxy, chlorine, bromine or iodine can be reacted with sodium sulfhydrate in an inert solvent, preferably a lower alkanol (i.e. methanol, ethanol and the like) to obtain the corresponding compound of formula I in which the corresponding $R^1$, $R^2$, $R^3$, $R^4$, $R^5$ and $R^6$ is mercapto. This reaction is preferably carried out at a temperature of from about −70° C to about 30° C for about 1 to 10 hours.

The following examples illustrate further this invention.

EXAMPLE I

[(2-Oxo-3,5,7-cycloheptatrien-1-yl)amino]oxo-acetic Acid Ethyl Ester; I ($R^1 = NH\text{-}CO\text{-}COOC_2H_5$ and $R^2$, $R^3$, $R^4$, $R^5$ and $R^6 = H$)

A solution of ethyl oxalyl chloride (0.30 g) in pyridine (15 ml) is added to a solution of 2-amino-2,4,6-cycloheptatrien-1-one [0.242 g, described by T. Nozoe et al., Proc. Japan Acad. 27, 556–560 (1951), CA 46, 7559 g] in pyridine (0.5 ml). The mixture is heated until a solution forms and the solution is stirred at room temperature for 45 minutes. Water is added and collection of the precipitate gives the title compound, mp 114° C.

In the same manner but replacing 2-amino-2,4,6-cycloheptatrien-1-one with an equivalent amount of 2-methylamino-2,4,6-cycloheptatrien-1-one [described by N. Soma et al., Chem. Pharm. Bull., 13, 457-64 (1965)], [N-(2-oxo-3,5,7-cycloheptatrien-1-yl)-N-methylamino]oxo-acetic acid ethyl ester, mp 70°–71° C, is obtained.

In the same manner but replacing ethyl oxalyl chloride with an equivalent amount of methyl or propyl oxalyl chloride, the methyl and propyl esters of the title compound are obtained.

EXAMPLE 2

[(3-Bromo-2-oxo-3,5,7-cycloheptatrien-1-yl)amino]oxo-acetic Acid Ethyl Ester; I ($R^1 = NH\text{-}CO\text{-}COOC_2H_5$; $R^2$, $R^3$, $R^4$ and $R^5 = H$ and $R^6 = Br$)

A solution of 7-bromo-2-methoxy-2,4,6-cycloheptatrien-1-one [1.0 g, described by T. Nozol et al., Proc. Japan Acad., 27, 556-60 (1951), (CA 46, 7560c)] in methanol (30 ml) is cooled to −20° C and saturated with gaseous ammonia. The reaction mixture is heated in a pressure bottle at 80° C for 4 hours and cooled to −70° C. The bottle is opened and the solvent is removed under reduced pressure. The residue is boiled with ethyl acetate and the ethyl acetate extract is evaporated to give 2-amino-7-bromo-2,4,6-cycloheptatrien-1-one.

A solution of the latter compound (0.800 g) in pyridine (10 ml) is cooled to 0° C and ethyl oxalyl chloride (0.544 g) is added dropwise. The mixture is stirred at 0° C for 1 hour and at room temperature for 2 hours. The solvent is removed under reduced pressure and the residue is crystallized from methanol-acetone to give the title compound, mp 161°–163° C.

In the same manner but replacing 7-bromo-2-methoxy-2,4,6-cycloheptatrien-1-one with an equivalent amount of 5-chloro-2-methoxy-2,4,6-cycloheptatrien-1-one [described by T. Sato, Nippon Kagaku Zasski, 80, 1171-4 (1959), (CA 55, 4389c)], [(5-chloro-2-oxo-3,5,7-cycloheptatrien-1-yl)amino]oxo-acetic acid ethyl ester, mp 178°–179° C, is obtained.

In the same manner but replacing ethyl oxalyl chloride with an equivalent amount of methyl or propyl oxalyl chloride, the methyl and propyl esters of the title compound are obtained.

EXAMPLE 3

[(3-Phenoxy-2-oxo-3,5,7-cycloheptatrien-1-yl)amino]-oxo-acetic Acid Ethyl Ester; 1 ($R^1$ = NH-CO-COOC$_2$H$_5$; $R^2$, $R^3$, $R^4$ and $R^5$ = H and $R^6$ = OC$_6$H$_5$)

a. A mixture of 2-hydroxy-3-phenoxy-2,4,6-cycloheptatrien-1-one [13.0 g, described by Y. Kitahara, Sci. Repts. Tohoku Univ. First Ser., 39, 265-74 (1956), (CA 51, 12874f)], potassium carbonate (28.9 g), dimethylsulfate (26.5 g) and methyl ethyl ketone (680 ml) is heated at reflux for two hours. The hot mixture is filtered and the filtrate is evaporated under reduced pressure. The residue is subjected to chromatography on silica gel using ether. The appropriate fractions of the eluate are combined and evaporated to give 2-methoxy-3-phenoxy-2,4,6-cycloheptatrien-1-one and 2-methoxy-7-phenoxy-2,4,6-cycloheptatrien-1-one.

b. A solution of 2-methoxy-7-phenoxy-2,4,6-cycloheptatrien-1-one (2.0 g, described above) in methanol (30 ml) is cooled to −25° C and saturated with gaseous ammonia. The mixture is heated in a pressure bottle at 80° C for 4 hours and cooled to −70° C. The bottle is opened and the solvent is removed under reduced pressure. The residue is crystallized from ethyl acetate to give 2-amino-7-phenoxy-2,4,6-cycloheptatrien-1-one.

In the same manner but replacing 2-methoxy-7-phenoxy-2,4,6-cycloheptatrien-1-one with an equivalent amount of 2-methoxy-3-phenoxy-2,4,6-cycloheptatrien-1-one [described above in (a)], 2-amino-3-phenoxy-2,4,6-cycloheptatrien-1-one is obtained.

c. A solution of 2-amino-7-phenoxy-2,4.6-cycloheptatrien-1-one [1.38 g, described above in (b)] in pyridine (50 ml) is cooled to 0° C and ethyl oxalyl chloride (0.980 g) is added dropwise. The mixture is stirred at 0° C for 1 hour and at room temperature for 2 hours. Most of the solvent is removed under reduced pressure and water (200 ml) is added. The precipitate is collected and crystallized from ethyl acetate to give the title compound, mp 145°-145.5° C.

In the same manner but replacing ethyl oxalyl chloride with an equivalent amount of methyl or propyl oxalyl chloride, the methyl and propyl esters of the title compound are obtained.

In the same manner but replacing 2-amino-7-phenoxy-2-amino-3-phenoxy-2,4,6-cycloheptatrine-1-one [described above in (b))], [(7-phenoxy-2-oxo-3,5,7-cycloheptatrien-1-one yl)amino]oxo-acetic acid ethyl ester, mp 121°-122° C, is obtained.

EXAMPLE 4

(5-Hydroxy-4-oxo-2,5,7-cycloheptatrien-1-yl)amino]oxo-acetic Acid Ethyl Ester; I ($R^1$ = OH, $R^2$, $R^3$, $R^5$ and $R^6$ = H and $R^4$ =NH-CO-COOC$_2$H$_5$)

Ethyl oxalyl chloride (1.36 g) is added dropwise to a solution at 0° C of 5-amino-2-hydroxy-2,4,6-cycloheptatrien-1-one [0.680 g, described by T. Nozoe et al., Sci. Repts. Tohoku Univ. 1, 35, 274-82 (1952)] in pyridine (15 ml). After 30 min. the reaction mixture is allowed to reach room temperature. The solvent is removed under reduced pressure and the residue is dissolved in methylene chloride. The solution is washed with water, dried, evaporated and the residue is crystallized from ethyl acetate to give the title compound, mp 186°-187° C.

In the same manner but replacing ethyl oxalyl chloride with an equivalent amount of ethyl oxalyl bromide, the title compound is obtained.

In the same manner but replacing ethyl oxalyl chloride with an equivalent amount oxalyl chloride or propyl oxalyl bromide [(5-hydroxy-4-oxo-2,5,7-cycloheptatrien-1-yl]amino]oxo-acetic acid methyl ester and [(5-hydroxy-4-oxo-2,5,7-cycloheptatrien-1-yl)amino]oxo-acetic acid propyl ester are obtained respectively.

EXAMPLE 5

[(3-Hydroxy-2-oxo-3,5,7-cycloheptatrien-1-yl)amino]-oxo-acetic Acid Ethyl Ester; 1 ($R^1$ = NH−CO−COOC$_2$H$_5$; $R^2$, $R^3$, $R^4$ and $R^5$ = H and $R^6$ = OH The hot solutions of 3-bromo-2-hydroxy-2,4,6-cycloheptatriene-1-one (30.0 g) in methanol (2000 ml) and cupric accetate (18.0 g) in methanol (2000 ml) are mixed and the precipitate is collected to give 3-bromo-2-hydroxy-2,4,6-cycloheptatrien-1 -one copper complex.

A mixture of the latter compound (11.65 g), potassium p-toluenesulfonamide (15.7 g) and pyridine (150 ml) is heated at reflux for 16 hours. The pyridine is evaporated under reduced pressure and chloroform is added to the residue. The precipitate is collected and washed with chloroform. The precipitate is suspended in chloroform and 2N sulfuric acid (40 ml) followed by the addition of hydrogen sulfide gas until the copper complex is decomposed. The precipitate is removed by filtration and the organic phase of the filtrate is separated. The organic phase is dried over sodium sulfate and evaporated. The residue is mixed with methanol and the precipitate is collected to obtain 2-hydroxy-3-[[(4-methylphenyl)sulfonyl]amino]-2,4,6-cycloheptatrien-1-one, mp 177°-179° C.

A solution of the latter compound (5.0 g) in conc. sulfuric acid (25 ml) is stirred at room temperature for 16 hours. The solution is poured on ice, neutralized with sodium carbonate and extracted with chloroform. The solvent is removed by evaporation to give a residue of 3-amino-2-hydroxy-2,4,6-cycloheptatrien-1-one [the latter compound is described in Sci. Repts. Tohoku Univ. First Ser., 39, 83-91 (1956)].

To a solution of the latter compound (1.19 g) and triethylamine (1.1 g) in methylene chloride (25 ml) at room temperature, ethyl oxalyl chloride (1.27 g) in methylene chloride (5 ml) is added dropwise. The mixture is stirred for four hours and washed with water. The organic phase is dried over sodium sulfate and evaporated. The residue crystallized from ethyl acetate to give the title compound, mp 158°-159° C.

In the same manner but replacing ethyl oxalyl chloride with an equivalent amount of methyl or propyl oxalyl chloride, the methyl and propyl esters of the title compound are obtained.

EXAMPLE 6

2,2'[(2-Oxo-3,5,7-cycloheptatrien-1,5-diyl)diimino]-bis[2-oxo-acetic acid] Diethyl Ester; I ($R^1$ and $R^4$ = NH−CO−COOC$_2$H$_5$ and $R^2$, $R^3$, $R^5$ and $R^6$ = H)

Conc. ammonium hydroxide solution (50 ml) is added dropwise to a suspension of 2-hydroxy-5-nitroso-2,4,6-cycloheptatrien-1-one [10 g, described by T. Nozoe et al., Sci. Repts. Tohoku Univ., 35, 274–82 (1952), (CA 47 3291a)] collected and washed with water then acetone to give 2-amino-5-nitroso-2,4,6-cycloheptatrien-1-one.

A mixture of the latter compound (5.0 g) and 5% palladium on charcoal (1.5 g) in ethanol (2000 ml) is stirred rapidly under an atmosphere of hydrogen for 12 minutes (hydrogen absorbed is 1600 ml). The mixture is filtered and the filtrate is evaporated to give 2,5-diamino-2,4,6-cycloheptatrien-1-one.

The latter compound is dissolved in pyridine (150 ml), cooled to 0° C and ethyl oxalyl chloride (9.55 g) is added dropwise. The reaction mixture is warmed to room temperature and stirred for two hours. Half of the pyridine is evaporated under reduced pressure and the residue is added to water (400 ml). The precipitate is collected, crystallized from ethyl acetate and subjected to chromatography on silica gel using ethyl acetate for elution. The eluates are evaporated and the residue is crystallized from ethyl acetate to give the title compound, mp 217°–218° C.

In the same manner but replacing ethyl oxalyl chloride with an equivalent amount of methyl or propyl oxalyl choride, the methyl and propyl esters of the title compound are obtained.

EXAMPLE 7

[(6-Methoxy-2-oxo-3,5,7-cycloheptatrien-1-yl)amino]-oxo-acetic Acid Ethyl Ester; I ($R^1$ = NH-CO-COOC$_2$H$_5$; $R^2$, $R^4$, $R^5$ and $R^6$ = H and $R^3$ = OCH$_3$)

a. A solution of 3-bromo-2-hydroxy-2,4,6-cycloheptatrien-1-one [27.5 g, described by T. Toda et al., Nippon Hagaku Zasshi, 88, 1234–5 (1967), (CA 68 101342)] and sodium methoxide (prepared from 12.6 g of sodium in methanol followed by evaporation of the methanol) in dimethyl sulfoxide (300 ml) is heated at 80° C for 1 hour. The solution is cooled poured on ice, acidified with 2N sulfuric acid and extracted with ethyl acetate. The organic extract is washed with brine, dried over sodium sulfate and evaporated. The residue is crystallized from ethyl acetate-hexane to give 2-hydroxy-3-methoxy-2,4,6-cycloheptatrien-1-one. Evaporation of the mother liquors gives 2-hydroxy-4-methoxy-2,4,6-cycloheptatrien-1-one.

b. A mixture of 2-hydroxy-4-methoxy-2,4,6-cycloheptatrien-1-one (described above, 13 g), potassium carbonate (23.6 g), dimethyl sulfate (21.6 g) and 2-butanone (130 ml) is heated at reflux for 3 hours. The mixture is filtered and the filtrate is evaporated. The residue is subjected to chromatography on silica gel using acetone-ethyl acetate (1:1) and evaporation of the eluates gives 2,4-dimethoxy-2,4,6-cycloheptatrien-1-one and 2,6-dimethoxy-2,4,6-cycloheptatrien-1-one.

In the same manner but replacing 2-hydroxy-4-methoxy-2,4,6-cycloheptatrien-1-one with an equivalent amount of 2-hydroxy-3-methoxy-2, 4,6-cycloheptatrien-1-one [(described above in (a)], 2,3-dimethoxy-2,4,6-cycloheptatrine-1-one and 2,7-dimethoxy-2,4,6-cycloheptatrine-1-one are obtained.

c. A solution of 2,4-dimethoxy-2,4,6-cycloheptatrien-1-one [described above in (b),2.4 g] in methanol (70 ml) is cooled to −25° C and saturated with ammonia gas. The solution is heated in a pressure bottle at 80° C for 4 hours and cooled to −70° C. The pressure bottle is opened and the solvent is evaporated to give 2-amino-4-methoxy-2,4,6-cycloheptatrien-1-one.

In the same manner but replacing 2,4-dimethoxy-2,4,6-cycloheptatrien-1-one with an equivalent amount of 2,6-dimethoxy-2,4,6-cycloheptatrien-1-one with an equivalent amount of 2,6-dimethoxy-2,4,6cycloheptatrien-1-one or 2,3-dimethoxy-2,4,6-cycloheptatrien-1one, 2-amino-6-methoxy-2,4,6-cycloheptatrien-1-one and 2-amino-3-methoxy-2,4,6-cycloheptatrien-1-one are obtained, respectively.

d. A solution of ethyl oxalyl chloride (2.16 g) in methylene chloride (25 ml) is added dropwise to a solution of 2-amino-4-methoxy-2,4,6-cycloheptatrien-1-one [described above in (c), 2.9 g] and triethylamine (1.84 g) in methylene chloride (50 ml). The mixture was stirred at room temperature for 3 hours, washed with water, dried over sodium sulfate and evaporated. The residue is subjected to chromatography on silica gel using ethyl acetate-hexane (2:3). The eluates are evaporated to give the title compound, mp 132°–134° C.

In the same manner but replacing ethyl oxalyl chloride with an equivalent amount of methyl or propyl oxalyl chloride, the methyl and propyl esters of the title compound are obtained.

In the same manner but replacing 2-amino-4-methoxy-2,4,6-cycloheptatrien-1-one with an equivalent amount of 2-amino-6-methoxy-2,4,6-cycloheptatrien-1-one or 2-amino-3-methoxy-2,4,6-cycloheptatrien-1-one, [(4-methoxy-2-oxo-3,5,7-cycloheptatrien-1-yl)amino]oxo-acetic acid ethyl ester, mp 157°–158° C, and [(7-methoxy-2-oxo-3,5,7-cycloheptatrien-1-yl)amino]oxo-acetic acid ethyl ester are obtained, respectively.

In the same amount but replacing dimethyl sulfate with an equivalent amount of diethyl sulfate, [(6-ethoxy-2-oxo-3,5,7-cycloheptatrien-1yl)amino]oxo-acetic acid ethyl ester is obtained.

EXAMPLE 8

[[7-Oxo-4-[(2-carboxyphenyl)thio]-1,3,5-cycloheptatrien-1-yl]amino]oxoacetic acid Ethyl Ester; I ($R^1$ = NH-CO-COOC$_2$H$_5$; $R^2$, $R^3$, $R^5$ and $R^6$ = H and $R^4$ = 2-carboxyphenylthio)

A solution of 5-[(2-carboxyphenyl)thio]-2-methoxy-2,4,6-cycloheptatrien-1-one (1.0 g, prepared from 5-chloro-2-methoxy-2,4,6-cycloheptatrien-1-one and 2-mercaptobenzoic acid) in methanol (30 ml) at −25° C is saturated with ammonia gas. The solution is heated in a pressure bottle at 80° C for 8 hours and cooled to −70° C. The bottle is opened and the solvent is evaporated to give 2-amino-5-[(2-caboxyphenyl)thio]-2,4,6-cycloheptatrien-1-one.

A solution of ethyl oxalyl chloride (1.0 g) in methylene chloride (10 ml) is added dropwise to a suspension of 2-amino-5-[(2-carboxyphenyl)thio]-2,4,6-cycloheptatrien-1-one (1.0 g) and triethylamine (0.74 g) in methylene chloride (30 ml). The mixture is stirred at room temperature for 30 minutes, washed with water, dried over sodium sulfate and evaporated. The residue is crystallized from ethyl acetate to give the title compound, mp 225°–228° C.

In the same manner but replacing 2-amino-5-[(2-carboxyphenyl)thio]-2,4,6-cycloheptatrien-1-one with an equivalent amount of 5-amino-2-[(2-carboxyphenyl)thio]-7-methyl-2,4,6-cycloheptatrien-1-one or 2-methylamino-6-[(2-carboxyphenyl)thio]-4-phenyl-2,4,6-cycloheptarien-1-one, [[5-oxo-4-[(2-carboxyphenyl)thio]-6-methyl-1,3,6-cycloheptatrien-1-yl]-amino]oxoacetic acid ethyl ester and [N-[7-oxo-5-[(2-carboxyphenyl)thio]-3-phenyl-1,3,5-cycloheptatrien-1-yl]-N- methylamino]oxo-acetic acid ethyl are obtained, respectively.

EXAMPLE 9

[[3-[N-[(4-Methylphenyl)sulfonyl]-N-methylamino]-2-oxo-3,5,7-cycloheptatrien-1-yl]amino]oxo-acetic Acid Ethyl Ester; I [$R^1$ = NH-CO-COOC$_2$H$_5$; $R^2$, $R^3$, $R^4$ and $R^5$ = H and $R^6$ = [N-(4-methylphenyl)sulfonyl]-N-methylamino]

a. A mixture of 2-hydroxy-3-[N-[(4-methylphenyl)sulfonyl]-amino]-2,4,6-cycloheptatrien-1-one (14.5 g), potassium carbonate (12.5 g), dimethyl sulfate (12.5 g) and 2-butanone (145 ml) is heated at reflux for 1 hour. The mixture is filtered and the precipitate is washed with water and suspended in ethyl actate. Hydrochloric acid (10%) is added until the solution is acidic. The organic phase is collected and dried over sodium sulfate. Evaporation of the solvent and crystallization of the residue from ethyl acetate-hexane gives 2-methoxy-7-[N-[(4-methylphenyl)sulfonyl]amino]-2,4,6-cycloheptatrien-1-one, mp 163°-164° C. The above filtrate is evaporated and the residue is subjected to chromatography on silica gel using ethyl acetate-hexane (3:1). Evaporation of the eluates are crystallization of the residue from ethyl acetate gives 2-methoxy-3-[N-[(4-methylphenyl)sulfonyl]-N-methylamino]-2,4,6-cycloheptatrien-1-one, mp 101°-102° C and 2-methoxy-7-[N-[(4-methylphenyl)sulfonyl]-N-methylamino]-2,4,6-cycloheptatrien-1-one, mp 94.5° C.

b. A solution at −25° C of 2-methoxy-7-[N-[(4-methylphenyl)sulfonyl]-N-methylamino]-2,4,6cycloheptatrien-1-one (described above, 4.0 g) in methanol (40 ml) is saturated with ammonia gas and heated in a pressure bottle at 80° C for 4 hours. The solution is cooled to −70° C, the bottle is opened and the solvent is evaporated to yield 2-amino-7-[N-[(4-methylphenyl)-sulfonyl]-N-methylamino]-2,4,6-cycloheptatrien-1-one, mp 221°-222° C.

In the same manner but replacing 2-methoxy-7-[N-[(4-methylphenyl)sulfonyl]-N-methylamino]-2,4,6-cycloheptatrien-1-one with an equivalent amount of 2-methoxy-7-[N-[(4-methylphenyl)sulfonyl]-amino]-2,4,6-cycloheptatrien-1-one or 2-methoxy-3-[N-[(4-methylphenyl)-sulfonyl]-N-methylamino]-2,4,6-cycloheptatrien-1-one, 2-amino-7-[N-[(4-methylphenyl)sulfonyl]amino]-2,4,6-cycloheptatrien-1-one and 2-amino-3-[N-[(4-methylphenyl)sulfonyl]-N-methylamino]-2,4,6-cycloheptatrien-1one are obtained respectively.

c. A solution of ethyl oxalyl chloride (0.475 g) in methylene chloride (10 ml) is added dropwise to a solution of 2-amino-7-[N-[(4-methylphenyl)sulfonyl]-N-methylamino]-2,4,6-cycloheptatriene-1-one (described above, 0.87 g) and triethylamino (0.354 g) in methylene chloride (10 ml). The solution is stirred at room temperature for 2 hours, washed with water, dried over sodium sulfate and evaporated. The residue is crystallized from ethyl acetate-hexane to give the title compound, mp 148.5°-150° C.

In the same manner but replacing ethyl oxalyl chloride with an equivalent amount of methyl or propyl oxalyl chloride, the methyl and propyl esters of the title compound are obtained.

In the same manner but replacing 2-amino-7-[N-[(4-methylphenyl)sulfonyl]-N-methylamino]-2,4,6-cycloheptatrien-1-one with an equivalent amount of 2-amino-7-[N-[(4-methylphenyl)sulfonyl]amino]-2,4,6-cycloheptatrien-1-one or 2-amino-3-[N-[(4-methylphenyl)sulfonyl]-N-methylamino]-2,4,6-cycloheptatrien-1-one, [[3-[N-[(4-methylphenyl)sulfonyl]amino]-2-oxo-3,5,7-cycloheptatrien-1-yl]amino]oxo-acetic acid ethyl ester and [[7-[N-[(4-methylphenyl)sulfonyl]-N-methylamino]-2-oxo-3,5,7-cycloheptatrien-1-yl]amino]-oxo-acetic acid ethyl ester are obtained respectively.

In the same manner but replacing dimethyl sulfate with an equivalent amount of diethyl sulfate, the title compound is obtained.

EXAMPLE 10

[(3-Methylamino-2-oxo-3,5,7-cycloheptatrien-1-yl)amino]oxo-acetic Acid Ethyl Ester; I ($R^1$ = NH-CO-COOC$_2$H$_5$; $R^2$, $R^3$, $R^4$ and $R^5$ = H and $R^6$ = NHCH$_3$)

A solution of 2-amino-7-[N-[(4-methylphenyl)sulfonyl]-N-methylamino]-2,4,6-cycloheptatrien-1-one [described in Example 9 (b), 2.53 g] in conc. sulfuric acid (25 ml) is heated at 75° C for 1 hour and added to ice. The ice-mixture is neutralized with sat. sodium carbonate solution and extracted with chloroform. The organic extract is dried over sodium sulfate and evaporated to give 2-amino-7-methylamino-2,4,6-cycloheptatrien-1-one.

A solution of ethyl oxalyl chloride (2.46 g) in methylene chloride (10 ml) is added dropwise to a solution of 2-amino-7-methylamino-2,4,6-cycloheptatrien-1-one (1.32 g) and triethylamine (1.95 g) in methylene chloride (15 ml). The mixture is heated at reflux for 3 hours, washed with water, dried over sodium sulfate and evaporated. The residue is subjected to chromatography on silica gel using acetone-hexane (3:7) and the eluates are evaporated to give the title compound, mp 178°-181° C.

In the same manner but replacing ethyl oxalyl chloride with an equivalent amount of methyl or propyl oxalyl chloride, the methyl and propyl esters of the title compound are obtained.

In the same manner but replacing 2-amino-7-[N-[(4-methylphenyl)sulfonyl]-N-methylamino]-2,4,6-cycloheptatrien-1-one with an equivalent amount of 2-methoxy-7-[N-[(4-methylphenyl)sulfonyl]amino]-2,4,6-cycloheptatrien-1-one [described in Example (9a)],[(3-methoxy-2-oxo-3,5,7-cycloheptatrien-1-yl)amino]oxo-acetic acid ethyl ester, mp 164°-167° C, is obtained.

By following a procedure selected from Examples 1 to 10 using the appropriate starting material of formula II and the appropriate compound of formula III in which $R^{10}$ is lower alkyl, other compounds of formula I in which at least one of $R^1$ and $R^4$ is NR$^9$COCOOR$^{10}$ wherein $R^9$ is as defined herein and $R^{10}$ is lower alkyl are obtained. Examples of the latter compounds of formula I are listed as products in Table I together with the appropriate starting material of formula II used for the preparation of the compound of formula I.

TABLE 1

| Ex. | $R^{11}$ | $R^{12}$ | $R^{13}$ | $R^{14}$ | $R^{15}$ | $R^{16}$ | Product: [(prefix listed below)-cycloheptatrien-1-yl)amino]-oxo-acetic acid (suffix listed below)] Prefix/Suffix |
|---|---|---|---|---|---|---|---|
| 11 | H | H | H | $NH_2$ | Br | $CH_3$ | [(2-bromo-3-methyl-4-oxo-2,5,7 // ethyl ester |
| 12 | $NHCH_3$ | H | $CH_3$ | H | $C_6H_5$ | H | [N-methyl-N-(6-methyl-2-oxo-4-phenyl-3,5,7 // ethyl ester |
| 13 | $NH_2$ | H | H | $OC_2H_5$ | H | I. | [(5-ethoxy-3-iodo-2-oxo-3,5,7 // methyl ester |
| 14 | $NH_2$ | H | H | $NHCH_3$ | $CH_3$ | H | [[5-[N-(2-ethoxy-1,2-dioxoethyl)methylamino]-4-methyl-2-oxo-3,5,7// ethyl ester |
| 15 | H | $C_3H_7$ | H | $NH_2$ | H | $CF_3$ | [(2-oxo-7-propyl-3-trifluoromethyl-3,5,7 // methyl ester |
| 16 | $NH_2$ | $C_5H_{11}$ | H | H | H | $OC_3H_7$ | [(2-oxo-7-pentyl-3-propoxy-3,5,7 // propyl ester |
| 17 | $NHC_3H_9$ | H | OH | F | H | H | [N-butyl-N-(5-fluoro-6-hydroxy-2-oxo-3,5,7 // propyl ester |
| 18 | $NHC_3H_7$ | H | H | $NH_2$ | H | $OC_6H_5$ | [[5-[N-(2-ethoxy-1,2-dioxoethyl)propylamino]-4-oxo-3-phenoxy-1,5,7// ethyl ester |
| 19 | $OC_2H_5$ | H | $C_4H_9$ | $NHC_2H_5$ | H | H | [N-ethyl-N-(7-butyl-5-ethoxy-4-xo-2,5,7 // methyl ester |
| 20 | H | $OCH_3$ | H | $NH_2$ | H | OH | [(3-hydroxy-6-methoxy-4-oxo-2,5,7 // ethyl ester |
| 21 | H | SH | H | $NH_2$ | $C_2H_5$ | H | [(2-ethyl-6-mercapto-4-oxo-2,5,7 // propyl ester |
| 22 | $NH_2$ | H | Cl | H | OH | H | [(6-chloro-4-hydroxy-2-oxo-3,5,7 // ethyl ester |
| 23 | $NHC_4H_9$ | H | $OC_6H_5$ | H | H | SH | [N-butyl-N-(3-mercapto-2-oxo-6-phenoxy-3,5,7 // methyl ester |
| 24 | $CF_3$ | Br | H | $NH_2$ | H | H | [(6-bromo-4-oxo-5-trifluoromethyl-2,5,7 // ethyl ester |
| 25 | $NH_2$ | H | H | $N(CH_3)_2$ | Cl | H | [(4-chloro-5-dimethylamino-2-oxo-3,5,7 // ethyl ester |
| 26 | $NH_2$ | H | $OC_2H_5$ | H | H | $N(C_3H_7)_2$ | [(6-ethoxy-3-dipropylamino-2-oxo-3,5,7 // methyl ester |
| 27 | $N(C_2H_5)_2$ | $CH_3$ | OH | $NH_2$ | H | H | [(5-diethylamino-7-hydroxy-6-methyl-4-oxo-2,5,7 // ethyl ester |
| 28 | $NH_2$ | SH | H | H | $N(CH_3)(C_2H_5)$ | H | [[4-(N-ethyl-N-methylamino)-7-mercapto-2-oxo-3,5,7 // propyl ester |

EXAMPLE 29

[(5-Methoxy-4-oxo-2,5,7-cycloheptatrien-1-yl)amino]-oxo-acetic Acid Methyl Ester; I ($R^1$ = $OCH_3$; $R^2$, $R^3$, $R^5$ and $R^6$ = H and $R^4$ = NH-CO-COOCH$_3$)

[(5-Hydroxy-4-oxo-2,5,7-cycloheptatrien-1-yl)amino]oxo-acetic acid ethyl ester (4.1 g, described in Example 4) is dissolved in boiling methanol (500 ml) and the mixture is cooled to room temperature and reacted with a solution of diazomethane in ether (ca. 351 ml). The reaction mixture is stirred for one hour until all the solid is reacted with diazomethane. The solvent is removed under reduced pressure and the residue is crystallized from methanol to give the title compound, mp 198°–200° C.

In the same manner but replacing [(5-hydroxy-4-oxo-2,5,7-cycloheptatrien-1-yl)amino]oxo-acetic acid ethyl ester with an equivalent amount of [(3-hydroxy-2-oxo-3,5,7-cycloheptatrien-1-yl)amino]oxo-acetic acid ethyl ester (described in Example 5), [(3-methoxy-2-oxo-3,5,7-cycloheptatrien-1-yl)amino]oxo-acetic acid methyl ester is obtained.

EXAMPLE 30

[(2-Oxo-3,5,7-cycloheptatrien-1-yl)amino]oxo-acetic Acid; I ($R^1$ = NH-CO-COOH and $R^2$, $R^3$, $R^4$, $R^5$ and $R^6$ = H)

A solution of potassium acetate (0.98 g) in water (5 ml) is added to a suspension of [(2-oxo-3,5,7-cycloheptatrien-1-yl)amino]oxo-acetic acid ethyl ester (2.21 g, described in Example 1) in water (15 ml) and the resulting mixture is heated at 100° C for 5 hours. The mixture is cooled, diluted with water, charcoalized and filtered. The filtrate is acidified with 10% hydrochloric acid and the precipitate is collected to give the title compound, mp 193°–194° C.

In the same manner but replacing potassium acetate with an equivalent amount of sodium bicarbonate or potassium carbonate, the title compound is obtained.

In the same manner but replacing the starting material [(2-oxo-3,5,7-cycloheptatrien-1-yl)amino]oxo-acetic acid ethyl ester with other esters of formula I, other acids of formula I are obtained. For example, replacing the starting material with the title compound of Examples 2,3,5,6,7,8,14 and 23, the following acids of formula I are obtained respectively: [(3-bromo-2-oxo-3,5,7-cycloheptatrien-1-yl)amino]oxo-acetic acid, [(3-phenoxy-2-oxo-3,5,7-cycloheptatrien-1-yl)amino]oxo-acetic acid, [(3-hydroxy-2-oxo-3,5,7-cycloheptatrien-1-yl)amino]oxo-acetic acid, 2,2'[(2-oxo-3,5,7-cycloheptatrien-1,5-diyl)diimino]bis[2-oxo-acetic acid], [(6-methoxy-2-oxo-3,5,7-cycloheptatrien-1-yl)amino]oxo-acetic acid, [(3-methylamino-2-oxo-3,5,7-cycloheptatrien-1-yl)amino]oxo-acetic acid, [[5-[N-(carboxycarbonyl)-N-methylamino]-4-methyl-2-oxo-3,5,7-cycloheptatrien-1-yl]amino]oxo-acetic acid and [N-(3-mercapto-2-oxo-6-phenoxy-3,5,7-cycloheptatrien-1-yl)-N-butylamino]oxo-acetic acid.

EXAMPLE 31

[(2-Oxo-3,5,7-cycloheptatrien-1-yl)amino]oxo-acetic Acid Pentyl Ester; I ($R^1$ = NH-CO-COOC$_5$H$_{11}$ and $R^2$, $R^3$, $R^4$, $R^5$ and $R^6$ = H)

A solution of [(2-oxo-3,5,7-cycloheptatrien-1-yl)amino]oxo-acetic acid (1.54 g, described in Example 30) and potassium carbonate (0.82 g) in dimethylsulfoxide (8 ml) is stirred at room temperature for 15 minutes. A solution of 5-bromopentane (1.52 ml) in dimethylsulfoxide (8 ml) is added and the resulting mixture is stirred at 80° C for 40 minutes. The mixture is cooled to room temperature and poured over ice. The mixture is stirred for ten minutes and the precipitate is collected by filtration. The precipitate is dissolved in ether, treated with charcoal and crystallized by the addition of hexane to give the title compound, mp 87°–89° C.

In the same manner but replacing the alkyl halide, 5-bromopentane, with an equivalent amount of 2-bromopropane or 2-bromo-2-methylpropane, [(2-oxo-3,5,7-cycloheptatrien-1-yl)amino]oxo-acetic acid 1-methylethyl ester, mp 91°–93° C and [(2-oxo-3,5,7-cycloheptatrien-1-yl)amino]oxo-acetic acid 1,1-dimethylethyl ester, mp 76°–78° C, are obtained respectively.

In the same manner but replacing the starting material, [(2-oxo-3,5,7-cycloheptatrien-1-yl)amino]oxo-acetic acid, with other acids of formula I and using an appropriate alkyl halide other esters of formula I are obtained. For example, replacing the starting material with an acid described in Example 30, the following esters of formula I are obtained. [(3-bromo-2-oxo-3,5,7-cycloheptatrien-1-yl)amino]oxo-acetic acid 2-methylpropyl ester, [(3-phenoxy-2-oxo-3,5,7-cycloheptatrien-1-yl)amino]oxo-acetic acid hexyl ester, 2,2'-[(2-oxo,3,5,7-cycloheptatrien-1,5-diyl)diimino]bis[2-oxo-acetic acid]dipropyl ester, [(6-methoxy-2-oxo-3,5,7-cycloheptatrien-1-yl)amino]oxo-acetic acid 1,1-dimethylethyl ester and [[5-[N-2-butoxy-1,2-dioxoethyl)-methyl amino]-4-methyl-2-oxo-3,5,7-cycloheptatrien-1-yl]amino]oxo-acetic acid butyl ester.

We claim:

1. A compound of formula I

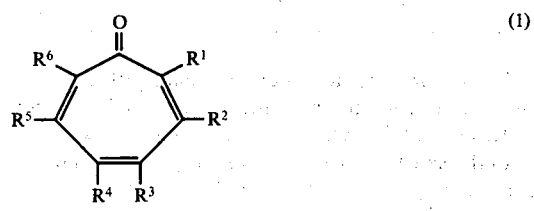

(1)

in which $R^1$ and $R^4$ are the same or different selected from the group consisting of hydrogen, halo, trifluoromethyl, lower alkoxy, lower alkyl, phenyl, hydroxy, phenoxy, mercapto, (2-carboxyphenyl)thio, $NR^7R^8$ wherein $R^7$ and $R^8$ each is hydrogen or lower alkyl or $R^7$ is lower alkyl and $R^8$ is p-toluenesulfonyl, and a radical of formula $NR^9COCOOR^{10}$ wherein $R^9$ and $R^{10}$ each is hydrogen or lower alkyl; and $R^2$, $R^3$, $R^5$ and $R^6$ are the same or different selected from the group consisting of hydrogen, halo, trifluoromethyl, lower alkoxy, lower alkyl, phenyl, hydroxy, phenoxy, mercapto, (2-carboxyphenyl)thio and $NR^7R^8$ wherein $R^7$ and $R^8$ each is hydrogen or lower alkyl or $R^7$ is lower alkyl and $R^8$ is p-toluenesulfonyl; with the proviso that at least one of $R^1$ and $R^4$ must be a radical of formula $NR^9COCOOR^{10}$ wherein $R^9$ and $R^{10}$ are as defined herein; or a therapeutically acceptable salt thereof.

2. A compound of formula 1

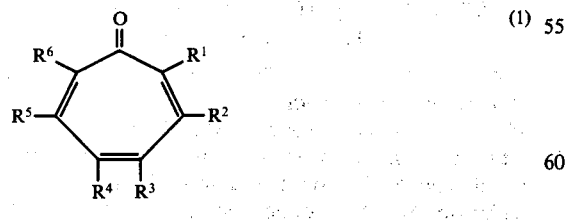

(1)

in which
a. $R^1$ is a radical of formula $NR^9COCOOR^{10}$ in which $R^9$ and $R^{10}$ each is hydrogen or lower alkyl, and $R^2$, $R^3$, $R^4$, $R^5$ and $R^6$ are the same or different selected from the group consisting of hydrogen, lower alkoxy and hydroxy;

b. $R^4$ is a radical of formula $NR^9COCOOR^{10}$ in which $R^9$ and $R^{10}$ each is hydrogen or lower alkyl, and $R^1$, $R^2$, $R^3$, $R^5$ and $R^6$ are the same or different selected from the group consisting of hydrogen, lower alkoxy and hydroxy; or c. $R^1$ and $R^4$ are a radical of formula $NR^9COCOOR^{10}$ wherein $R^9$ and $R^{10}$ each is hydrogen or lower alkyl, and $R^2$, $R^3$, $R^5$ and $R^6$ are the same or different selected from the group consisting of hydrogen, lower alkoxy and hydroxy; or a therapeutically acceptable salt thereof.

3. A compound of formula 1

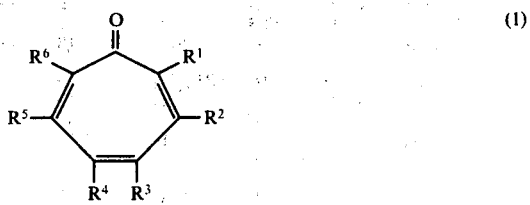

(1)

in which
a. $R^1$ is a radical of formula $NR^9COCOOR^{10}$ in which $R^9$ and $R^{10}$ each is hydrogen or lower alkyl, and $R^2$, $R^3$, $R^4$, $R^5$ and $R^6$ are the same or different selected from the group consisting of hydrogen, lower alkoxy and hydroxy, with the proviso that at least three of $R^2$, $R^3$, $R^4$, $R^5$ and $R^6$ are hydrogen;

b. $R^4$ is a radical of formula $NR^9COCOOR^{10}$ in which $R^9$ and $R^{10}$ each is hydrogen or lower alkyl, and $R^1$, $R^2$, $R^3$, $R^5$ and $R^6$ are the same or different selected from the group consisting of hydrogen, lower alkoxy and hydroxy, with the proviso that at least three of $R^1$, $R^2$, $R^3$, $R^5$ and $R^6$ are hydrogen; or c. $R^1$ and $R^4$ are a radical of formula $NR^9COCOOR^{10}$ wherein $R^9$ and $R^{10}$ each is hydrogen or lower alkyl, and $R^2$, $R^3$, $R^5$ and $R^6$ are the same or different selected from the group consisting of hydrogen, lower alkoxy and hydroxy, with the proviso that at least two of $R^2$, $R^3$, $R^5$ and $R^6$ are hydrogen, or a therapeutically acceptable salt thereof.

4. A compound of formula 1

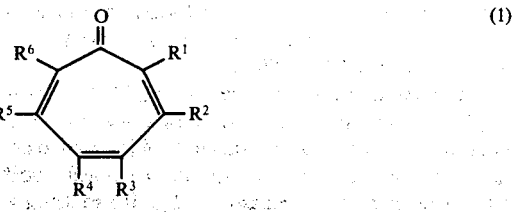

(1)

in which
a. $R^1$ is a radical of formula $NR^9COCOOR^{10}$ in which $R^9$ and $R^{10}$ each is hydrogen or lower alkyl, and $R^2$, $R^3$, $R^4$, $R^5$ and $R^6$ are hydrogen; or
b. $R^1$ and $R^4$ are a radical of formula $NR^9COCOOR^{10}$ in which $R^9$ and $R^{10}$ each is hydrogen or lower alkyl, and $R^2$, $R^3$, $R^5$ and $R^6$ are hydrogen, or a therapeutically acceptable salt thereof.

5. [(2-Oxo-3,5,7-cycloheptatrien-1-yl)amino]oxo-acetic acid ethyl ester, as claimed in claim 1.

6. [(2-Oxo-3,5,7-cycloheptatrien-1-yl)-N-methylamino]oxo-acetic acid ethyl ester, as claimed in claim 1.

7. [(3-Bromo-2-oxo-3,5,7-cycloheptatrien-1-yl)amino]oxo-acetic acid ethyl ester, as claimed in claim 1.

8. [(5-Chloro-2-oxo-3,5,7-cycloheptatrien-1-yl)amino]oxo-acetic acid ethyl ester, as claimed in claim 1.

9. [(3-Phenoxy-2-oxo-3,5,7-cycloheptatrien-1-yl)amino]oxo-acetic acid ethyl ester, as claimed in claim 1.

10. [(7-Phenoxy-2-oxo-3,5,7-cycloheptatrien-1-yl)amino]oxo-acetic acid ethyl ester, as claimed in claim 1.

11. [(5-Hydroxy-4-oxo-2,5,7-cycloheptatrien-1-yl)amino]oxo-acetic acid ethyl ester, as claimed in claim 1.

12. [(3-Hydroxy-2-oxo-3,5,7-cycloheptatrien-1-yl)amino]oxo-acetic acid ethyl ester, as claimed in claim 1.

13. 2,2'[(2-Oxo-3,5,7-cycloheptatrien-1,5-diyl)-diimino]bis[2-oxo-acetic acid] diethyl ester, as claimed in claim 1.

14. [(5-Methoxy-4-oxo-2,5,7-cycloheptatrien-1-yl)amino]oxo-acetic acid Methyl Ester, as claimed in claim 1.

15. [(2-Oxo-3,5,7-cycloheptatrien-1-yl)amino]oxo-acetic acid pentyl ester, as claimed in claim 1.

16. [(2-Oxo-3,5,7-cycloheptatrien-1-yl)amino]oxo-acetic acid 1-methylethyl ester, as claimed in claim 1.

17. [(2-Oxo-3,5,7-cycloheptatrien-1-yl)amino]oxo-acetic acid, 1,1-dimethylethyl ester, as claimed in claim 1.

18. [(2-Oxo-3,5,7-cycloheptatrien-1-yl)amino]oxo-acetic acid, as claimed in claim 1.

19. [[3-[N-[(4-Methylphenyl)sulfonyl]-N-methylamino]-2-oxo-3,5,7-cycloheptatrien-1-yl]amino]-oxo-acetic acid ethyl ester, as claimed in claim 1.

20. [(3-Methylamino-2-oxo-3,5,7-cycloheptatrien-1-yl)amino]oxo-acetic acid ethyl ester, as claimed in claim 1.

21. [(3-Methoxy-2-oxo-3,5,7-cycloheptatrien-1-yl)amino]oxo-acetic acid ethyl ester, as claimed in claim 1.

22. [(6-Methoxy-2-oxo-3,5,7-cycloheptatrien-1-yl)amino]oxo-acetic acid ethyl ester, as claimed in claim 1.

23. [(4-Methoxy-2-oxo-3,5,7-cycloheptatrien-1-yl)amino]oxo-acetic acid ethyl ester, as claimed in claim 1.

24. [[7-oxo-4-[(2-carboxyphenyl)thio]-1,3,5-cycloheptatrien-1-yl)amino]oxo-acetic acid ethyl ester, as claimed in claim 1.

25. A method for suppressing allergic manifestations of anaphylactic reactions and atopic hypersensitivity in a mammal which comprises administering to said mammal an effective amount of a compound of claim 1, or a therapeutically acceptable salt thereof.

26. A pharmaceutical composition useful in suppressing allergic manifestations of anaphylactic reactions and atopic hypersensitivity comprising a compound of claim 1, or a therapeutically acceptable salt thereof, and a pharmaceutically acceptable carrier.

* * * * *